United States Patent
Risch et al.

(10) Patent No.: US 10,500,032 B2
(45) Date of Patent: Dec. 10, 2019

(54) ENCAPSULATED ABSORBER AND TEMPORAL ACTIVATION THEREOF

(71) Applicant: BIOTRONIK AG, Buelach (CH)

(72) Inventors: Fabian Risch, Schaffhausen (CH); Matthias Wesselmann, Ruedlingen (CH); Stefan Wessbecher, Buelach (CH); Bodo Quint, Dettighofen (DE)

(73) Assignee: BIOTRONIK AG, Buelach (CH)

( * ) Notice: Subject to any disclaimer, the term of this patent is extended or adjusted under 35 U.S.C. 154(b) by 0 days.

(21) Appl. No.: 16/096,581

(22) PCT Filed: May 4, 2017

(86) PCT No.: PCT/EP2017/060682
§ 371 (c)(1),
(2) Date: Oct. 25, 2018

(87) PCT Pub. No.: WO2017/202589
PCT Pub. Date: Nov. 30, 2017

(65) Prior Publication Data
US 2019/0133741 A1    May 9, 2019

(30) Foreign Application Priority Data
May 23, 2016    (DE) .................... 10 2016 109 394

(51) Int. Cl.
*B65D 81/26*    (2006.01)
*A61F 2/00*    (2006.01)
(Continued)

(52) U.S. Cl.
CPC .......... *A61F 2/0095* (2013.01); *B65D 81/268* (2013.01); *A61B 50/30* (2016.02); *A61M 25/002* (2013.01)

(58) Field of Classification Search
CPC ..... B65D 81/268; A61F 2/0095; A61B 50/30; A61M 25/002
(Continued)

(56) References Cited

U.S. PATENT DOCUMENTS 3,967,728 A * 7/1976 Gordon ............... A61M 25/002
                                                    206/364
4,660,721 A * 4/1987 Mykleby .................. A61L 2/26
                                                    206/438

(Continued)

FOREIGN PATENT DOCUMENTS

EP          1867298 A1    4/2006
WO       2004066879 A1    8/2004

OTHER PUBLICATIONS

Colin Smith, International Search Report for Application No. PCT/EP2017/060682, dated Jun. 9, 2017.

*Primary Examiner* — Luan K Bui
(74) *Attorney, Agent, or Firm* — Greer, Burns & Crain, Ltd.; Steven P. Fallon

(57) ABSTRACT

Packaging has an outer sleeve, which surrounds an interior space for receiving an object, such as a sterilized medical implant. A separate container is arranged in the interior space and surrounds an absorber in a gas-tight manner, such that a gas present in the interior space cannot pass to the absorber. The container is configured to be opened by the application of force when the outer sleeve is closed, such that a gas disposed in the interior space can pass to the absorber and can be absorbed thereby. In preferred embodiments, the absorber absorbs air with the reactive constituents $O_2$ and/or $H_2O$. Depending on the application, however, other gases can also be absorbed by the absorber. A method for packaging is also provided.

11 Claims, 3 Drawing Sheets

(51) Int. Cl.
*A61B 50/30* (2016.01)
*A61M 25/00* (2006.01)

(58) Field of Classification Search
USPC .................................. 206/204, 438
See application file for complete search history.

(56) References Cited

U.S. PATENT DOCUMENTS

| | | | | |
|---|---|---|---|---|
| 6,530,471 | B1* | 3/2003 | Tsuyuguchi | B65D 81/264 |
| | | | | 206/204 |
| 7,025,205 | B2* | 4/2006 | Barker | B65D 75/26 |
| | | | | 206/205 |
| 7,631,760 | B2* | 12/2009 | Guelzow | A61F 2/0095 |
| | | | | 206/204 |
| 2001/0054562 | A1* | 12/2001 | Pettersson | B32B 27/08 |
| | | | | 206/364 |
| 2006/0186010 | A1* | 8/2006 | Warnack | A61M 25/002 |
| | | | | 206/438 |
| 2007/0289887 | A1* | 12/2007 | Murray | A61M 25/002 |
| | | | | 206/364 |
| 2013/0213827 | A1* | 8/2013 | Hammad | B65D 81/2023 |
| | | | | 206/204 |

\* cited by examiner

ENCAPSULATED ABSORBER AND TEMPORAL ACTIVATION THEREOF

PRIORITY CLAIM

This application is a 35 U.S.C. 371 US National Phase and claims priority under 35 U.S.C. § 119, 35 U.S.C. 365(b) and all applicable statutes and treaties from prior PCT Application PCT/EP2017/060682, which was filed May 4, 2017, which application claimed priority from German Application DE 102016109394.7, which was filed May 23, 2016.

FIELD OF THE INVENTION

The present invention relates to a packaging for packaging an object that is to be sterilized, in particular in the form of a stent or balloon (for example in the form of a stent delivering an active substance, i.e. a stent which is configured to release a drug in the implanted state). The invention also relates to a packaged medical implant and a method for packaging a medical implant or object that is to be sterilized.

BACKGROUND

An implant delivering an active substance, for example in the form of a stent or balloon, can change by its reaction with moisture and oxygen. In order to ensure the efficacy of the implant, it helps to remove gases of this type from the surrounding environment of the implant, for example by means of absorbers. During the production process, however, these gases are part of the surrounding environment (in particular during a gas sterilization, for example by means of ethylene oxide). Since the absorber components have a limited absorption capacity, they should thus only be exposed to the surrounding environment following the sterilization, since otherwise they would become saturated already during the production process.

An existing solution uses standardised absorber components with use of two separate pouches. With the use of two separate pouches, there is an inner gas-permeable pouch and an outer gas-permeable pouch. The product is packaged and sterilized in the inner gas-permeable pouch. The outer pouch is filled with the packaged and sterilized product and the absorber component and is then closed. In summary, the following disadvantages are encountered with the use of two pouches:

The end user has to open 2 pouches.
The outer side of the inner pouch is not sterile.
The packing process is more complex, thus incurring greater process costs.
Greater material costs.
More waste.
Larger storage volume necessary on account of larger packing volumes.

A further existing solution uses standardised absorber components with use of a specific pouch design. This pouch design has two chambers (a product chamber and an absorber chamber), which make it possible to add an absorber after sterilization without opening the product chamber. The gas exchange between absorber chamber and product chamber occurs via a porous membrane. Packagings of this type are known for example from U.S. Pat. No. 8,297,439 B2. A disadvantage of a pouch having two chambers is constituted generally by the additional material costs caused by a relatively complex pouch design with additional material layers. There is also more waste produced by the additional packaging material.

SUMMARY OF THE INVENTION

A preferred embodiment packaging has an outer sleeve, which surrounds an interior space for receiving an object, such as a sterilized medical implant. A separate container is arranged in the interior space and surrounds an absorber in a gas-tight manner, such that a gas present in the interior space cannot pass to the absorber. The container is configured to be open by the application of force when the outer sleeve is closed, such that a gas disposed in the interior space can pass to the absorber and can be absorbed thereby. In preferred embodiments, the absorber absorbs air with the reactive constituents $O_2$ and/or $H_2O$. Depending on the application, however, other gases can also be absorbed by the absorber.

A preferred method for packaging an object that is to be sterilized (in particular in the form of a medical implant, in particular a stent or balloon catheter, in particular a stent or balloon catheter delivering an active substance) includes providing and arranging a container that can be opened or destroyed by the application of force and also providing and arranging the object that is to be sterilized in an interior space of a packaging defined by an outer sleeve, wherein the container surrounds an absorber in a gas-tight manner. The object is sterilized (for example by applying a gas or an ionising radiation) before being placed in the interior space, after which the outer sleeve is closed. The container is then open, for example by applying force to the container, whilst the outer sleeve is closed, such that a gas disposed in the interior (for example $O_2$ and/or $H_2O$) is absorbed by the absorber.

BRIEF DESCRIPTION OF THE DRAWINGS

The invention will be explained in greater detail hereinafter on the basis of drawings and exemplary embodiments.

DETAILED DESCRIPTION OF THE PREFERRED EMBODIMENTS

Figure 1:
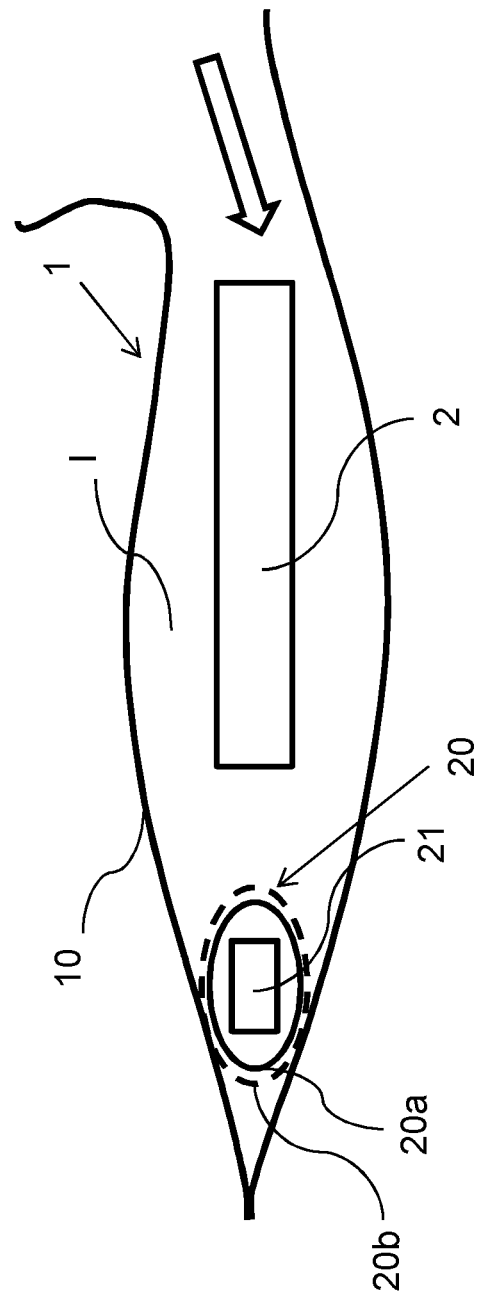
FIG. 1 shows an opened packaging or outer sleeve, wherein the container and the object that is to be sterilized are arranged in the interior space of the outer sleeve through an opening in the outer sleeve.

The outer sleeve in preferred embodiments can be a single part sleeve. The outer sleeve can also consist of a number of component parts. The outer sleeve is configured to be closed, for example once the container and the object have been arranged in the outer sleeve or the interior space formed by the outer sleeve. A further component part of the outer sleeve can be a breathable membrane, which allows the exchange of gases. This exchange is necessary for the sterilization of the object by gas. Once the outer sleeve has been closed prior to the sterilization, the interior space is delimited or completely enclosed outwardly by the outer sleeve.

The invention thus advantageously enables the addition of an absorber already before the sterilization by protection of the absorber from the surrounding environment until the point of activation of the absorption at an arbitrary moment in time.

Existing packaging components or systems can thus still be used. In addition, the absorbers can be easily handled during production, since they are initially packaged in a gas-tight manner and therefore do not have to be processed within a short space of time. Apart from the container of the absorber, there are in particular no further packaging chambers or pouches provided, and therefore a reduction of the waste usually accumulated is also possible.

As necessary, the solution according to the invention can lastly also be applied to other products in the field of medical engineering in addition to the above-mentioned stents or balloon catheters, these products being selected from the group comprising or consisting of: a biosensor, a dialysis unit, a drug delivery system, an electrode, a vascular cuff, a pacemaker, a cardiac pacemaker, a defibrillator, a cardioverter, a brain pacemaker, a neuroprosthetic, electrodes/electronics for artificial limbs, a nerve stimulator, a barostimulator, a kidney pacemaker, a duodenal pacemaker, a heart implant, a tumour-monitoring implant, an artificial heart, an artificial heart valve primarily with artificial or natural tissue, a shunt, a brain shunt, a hydrocephalus implant, an occluder, natural tissue, preferably dried natural tissue, a telemetry unit, a receiving unit, a transmitting unit, a pressure sensor, an organ replacement, an energy harvesting implant, a biofuel cell, a catheter, a cochlear implant, a retina implant, a dental implant, an artificial implantable lens system, an implant for joint replacement, and a vascular prosthesis; in particular if these implants comprise an antibacterial coating or a coating delivering an active substance. Contact lenses and bone implants, such as nails or screws, can also be packaged by the method proposed herein. However, the method herein according to the invention can also be used in other fields apart from the medical engineering, for example in the food or pharmaceutical industries.

The method proposed herein is particularly preferably used for implants, such as stents, balloon catheters and electrodes, comprising an active substance.

In accordance with an embodiment of the packaging according to the invention, it is provided that the container is formed as a rigid capsule or as a flexible pouch. Suitable materials that can be used include gas-tight polymers, for example ethylene-vinyl alcohol copolymer (EVOH) and polyvinylidene chloride (PVdC), or metals, for example aluminium. A container of this type, which does not have any further surrounding and gas-permeable sleeve, is usually sterilized in the known manner, for example by means of an ionising radiation or particle bombardment, prior to the insertion in the interior space of the outer sleeve or packaging.

In accordance with an embodiment of the packaging according to the invention, it is also provided that the container comprises an inner container (for example in the form of a capsule or a pouch, with barrier effect by gas-tight polymer, such as EVOH or PVdC, or metal, such as aluminium) surrounding the absorber in a gas-tight manner and also a gas-permeable sleeve surrounding the inner container. The gas-permeable sleeve is permeable for the gases to be absorbed in the interior of the packaging (for example $O_2$ and/or $H_2O$), and also for the gases of a sterilization. The gas-permeable sleeve nevertheless forms a barrier against a microbial contamination.

The gas-permeable sleeve in accordance with an embodiment of the invention can be produced for example from polyethylene (PE) or can comprise PE. In a preferred embodiment the sleeve can be manufactured from a non-woven, in particular Tyvek® from PE-HD (high-density polyethylene). Another material that can be used for a gas-permeable sleeve is paper.

As a result of this gas-permeable sleeve, the content of the gas-permeable sleeve does not have to be sterilized. When the inner container is opened, it is ensured by means of the microbial barrier properties of the gas-permeable sleeve that the object is not contaminated. In addition, a particle emission by the opening of the inner container is also prevented. By means of an appropriate design of the gas-permeable sleeve, it is possible to ensure that the gas-permeable sleeve is not opened or damaged when the inner container is opened.

In accordance with an embodiment of the packaging according to the invention it is also provided that the container is fixed in the interior space to the outer sleeve. For example, the container can be fixed to existing components of the packaging, for example to the inner surface of the outer sleeve or to a packaging ring which is typical for stent systems and which serves to receive the balloon catheter. The fixed positioning facilitates the later locating of the container when the outer sleeve is closed and thus the mechanical opening of the container.

In accordance with an embodiment of the packaging according to the invention it is also provided that the container has a specific form, such that a unique identification of the state of the container (closed (gas-tight) or open (permeable)) it is possible from outside, i.e. from the outer side of the outer sleeve. It is thus ensured that the absorber is activated at the desired moment in time (and not beforehand, for example). Here, the embodiment is particularly advantageous when the identification is provided haptically or visually.

A further aspect of the present invention relates to a packaged object, in particular a packaged medical implant, including a packaging according to the invention, wherein the object or the medical implant is arranged in the interior space formed by the outer sleeve.

In accordance with an embodiment of the object packaged in accordance with the invention, the medical implant is particularly preferably a stent, in particular a stent delivering an active substance, i.e. a stent that is configured to release a drug in the implanted state.

The container can be opened in different ways, for example by means of a mechanical force or by means of a negative pressure, which for example causes the container to burst. The container can also be opened by the influence of a force field or magnetic field or by irradiation of an effective energy, such as microwaves or infrared radiation.

In accordance with an embodiment of the method according to the invention the container receiving the absorber is sterilized before it is arranged in the interior space or the outer sleeve.

In accordance with an alternative embodiment of the method according to the invention it is provided that the container receiving the absorber has an inner container, which encloses the absorber in a gas-tight manner, and a gas-permeable sleeve surrounding the inner container, wherein the container is sterilized together with the object in the interior space.

The gas-permeable sleeve can consist of the materials or substances specified herein.

Figure 2:
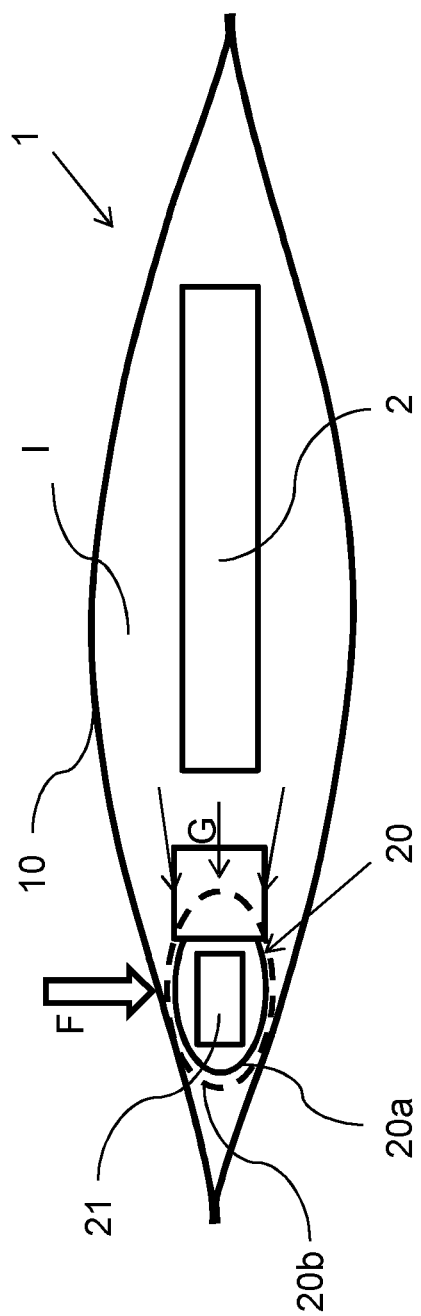
FIG. 2 shows the closed outer sleeve, which surrounds the sterilized container and the sterilized object, wherein the container is opened or destroyed by a force exerted from an outer side of the sleeve, such that the absorber can absorb gas disposed in the interior space, in particular $O_2$ and/or $H_2O$.

FIG. 1, in conjunction with FIG. 2, shows a packaging 1 according to the invention for an object 2 that is to be sterilized, which is preferably a medical implant, in particular an implant delivering an active substance, preferably a stent delivering an active substance. The packaging 1 comprises a gas-tight outer sleeve 10 which for example is at least partially or fully flexible (for example a film with barrier effect by gas-tight polymer, such as EVOH or PVdC, or metal, such as aluminium) and which surrounds or defines an interior space I of the packaging for receiving the object 2. The packaging 1 also has a container 20 arranged or formed in the interior space (I), which container surrounds an absorber 21 in a gas-tight manner, such that a gas G present in the interior space I, for example $O_2$ and/or $H_2O$, cannot pass to the absorber 21. The container 20 in accordance with one embodiment can also be an inner container 20a, which can be encased by a gas-permeable sleeve 20b (for example made of paper or a nonwoven, such as Tyvek®).

The container 20 or 20a is designed, when the outer sleeve 10 is closed, i.e. the outer sleeve in particular hermetically seals off the interior space outwardly, to be opened by application of force, such that a gas G disposed in the interior space I can pass to the absorber 21 and can be absorbed thereby. Said force can be exerted onto the container from the outside, i.e. through the outer sleeve or via the outer sleeve, for example manually by a person or by a machine.

The absorber can be a commercially available standard absorber (for example PharmaKeep KD-20 from MGC).

If a gas-permeable sleeve 20b is provided, the inner container 20a, which for example is formed as a capsule, is inserted into the interior space I of the packaging 1 together with the surrounding gas-permeable sleeve 20b prior to the sterilization together with the object 2 that is to be packaged or sterilized (for example a stent delivering active substance) (see FIG. 1).

After the sterilization of the object 2 and of the container 20, the capsule 20a is mechanically opened from outside (for example by the operator or also by a facility) and the absorption of the undesirable gases G in the interior space is thus started. The gas-permeable sleeve 20b is not destroyed hereby and is permeable for the gases G to be absorbed (for example $O_2$ and/or $H_2O$). In addition, the gas-permeable sleeve 20b in turn forms a mechanical barrier with respect to the object 2 for particles or similar material which could be released following the opening of the container 20 or 20a in the interior of 20b and could potentially come into contact with the object 2.

In accordance with an alternative embodiment the inner container 20a and the sleeve 20b can be replaced by an individual container 20, for example in the form of a closed and flexible pouch, which surrounds the absorber 21 in a gas-tight manner. The pouch 20 and content thereof are now sterilized for example by means of radiation sterilization. After the sterilization of the object 2, the pouch 20 is made to burst by means of a mechanical force or by means of negative pressure, such that the gases G (see above) in the interior space I can be absorbed. The pouch 20, when the outer sleeve 10 is closed or open, can be sterilized together with the object 2 under microbial barrier effect. The pouch 20 can be inserted into the interior space I or the outer sleeve 10 also in the sterilized state. The object 2 can then be sterilized subsequently in the open outer sleeve 10 (for example by means of gas sterilization) or in the closed outer sleeve (for example by means of radiation sterilization).

Figure 3:
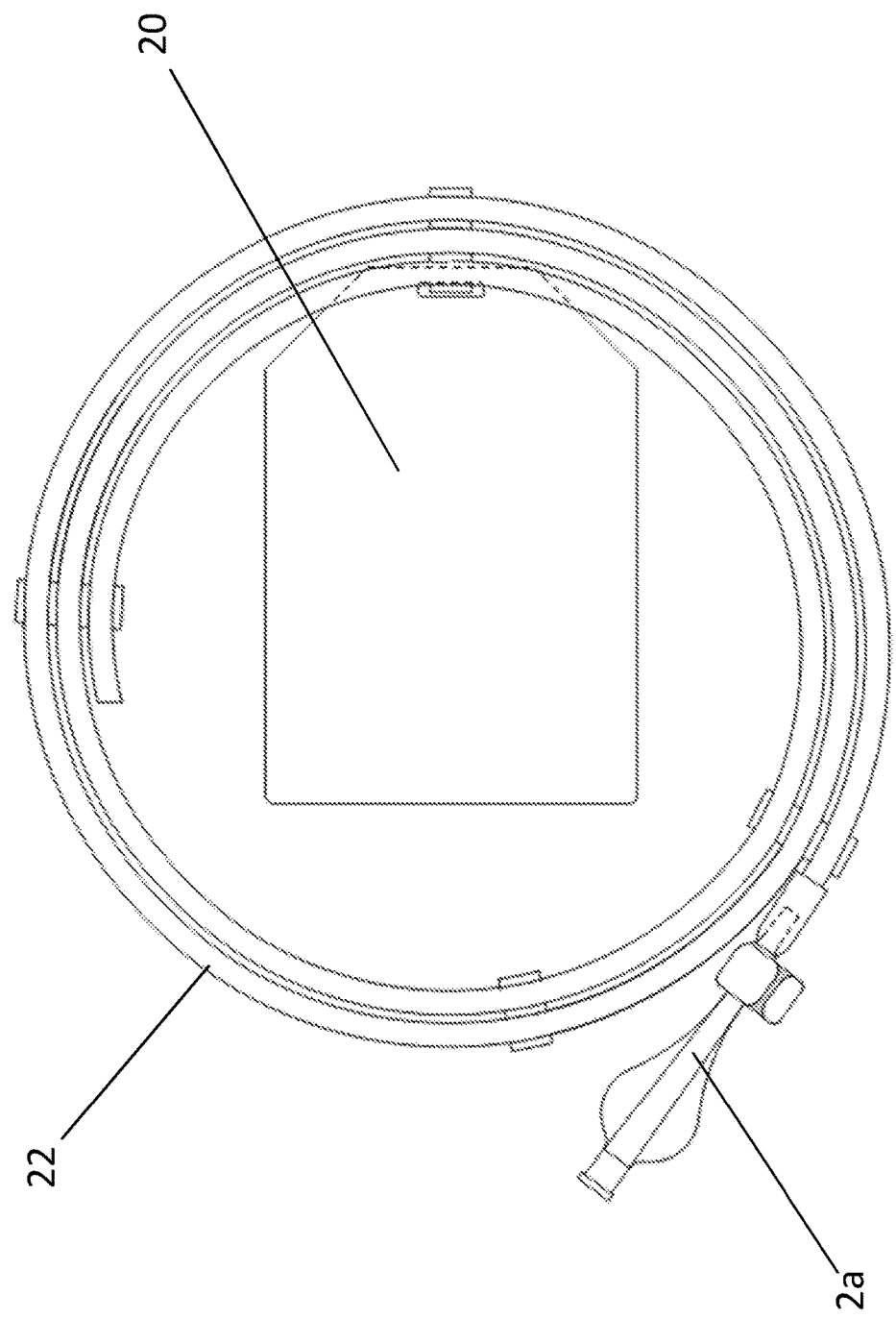
FIG. 3 shows an arrangement of the absorber container in the embodiment comprising a packaging ring.

FIG. 3 shows a further use of the packaging proposed here. The absorber container 20 is fixed here to a packaging ring 22, which serves to receive the balloon catheter 2a and which is typical for stent systems.

The invention claimed is:

1. A packaging for an object that is to be sterilized, said packaging comprising
    an outer sleeve surrounding an interior space sized and shaped to receive the object,
    a container arranged in the interior space and surrounding an absorber in a gas-tight manner, such that a gas present in the interior space cannot pass to the absorber, wherein the container is designed to be opened while the outer sleeve is closed with the object in the interior space, such that a gas disposed in the interior space can pass to the absorber and can be absorbed thereby.

2. The packaging according to claim 1, wherein the container is formed as a rigid capsule or as a flexible pouch.

3. The packaging according to claim 1, wherein the container comprises an inner container surrounding the absorber in a gas-tight manner and a gas-permeable sleeve surrounding the inner container.

4. The packaging according to claim 1, wherein the container is fixed in the interior space to the outer sleeve.

5. The packaging according to claim 1, wherein the container has a different form in an opened state and a closed state, in such a way that the state of the container can be determined haptically or visually through the surrounding outer sleeve.

6. A packaged object, comprising a packaging according to claim 1, wherein the packaged object is the object arranged in the interior space.

7. The packaged object according to claim 6, wherein the object is a medical implant.

8. A method for packaging an object that is to be sterilized, said method comprising the following steps:
    placing a container and the object in an interior space of an outer sleeve, wherein the container surrounds an absorber in a gas-tight manner,
    sterilizing the object before or after placing it in the outer sleeve and closing the outer sleeve after the sterilizing and the object being placed in the outer sleeve, and
    opening the container after the outer sleeve is closed such that a gas disposed in the interior space is absorbed by the absorber.

9. The method according to claim 8, wherein the container is sterilized before it is arranged in the interior space.

10. The method according to claim 8, wherein the container comprises an inner container, which encloses the absorber in a gas-tight manner, and also comprises a gas-permeable sleeve surrounding the inner container, wherein the container is sterilized together with the object in the interior space.

11. The method according to claim 8, wherein the opening comprises applying force to the container through the outer sleeve after the outer sleeve is closed.

* * * * *